United States Patent
Kimura et al.

(10) Patent No.: US 11,361,406 B2
(45) Date of Patent: Jun. 14, 2022

(54) IMAGE PROCESSING APPARATUS, IMAGE PROCESSING METHOD, AND NON-TRANSITORY COMPUTER READABLE RECORDING MEDIUM

(71) Applicant: OLYMPUS CORPORATION, Tokyo (JP)

(72) Inventors: Mitsutaka Kimura, Tokyo (JP); Masashi Hirota, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 853 days.

(21) Appl. No.: 16/218,671

(22) Filed: Dec. 13, 2018

(65) Prior Publication Data

US 2019/0122344 A1 Apr. 25, 2019

Related U.S. Application Data

(63) Continuation of application No. PCT/JP2016/071777, filed on Jul. 25, 2016.

(51) Int. Cl.
*G06T 7/00* (2017.01)
*G06T 5/00* (2006.01)
(Continued)

(52) U.S. Cl.
CPC .......... *G06T 5/002* (2013.01); *A61B 1/00009* (2013.01); *A61B 1/00045* (2013.01);
(Continued)

(58) Field of Classification Search
CPC ........... G06T 5/002; G06T 5/009; G06T 5/50; G06T 2207/10016; G06T 2207/10024;
(Continued)

(56) References Cited

U.S. PATENT DOCUMENTS 9,173,554 B2* 11/2015 Fengler .................... A61B 1/04
2013/0286172 A1* 10/2013 Sasaki ................ A61B 1/00188
348/65

(Continued)

FOREIGN PATENT DOCUMENTS

| JP | 2012-135345 A | 7/2012 |
| WO | WO 2013/018575 A1 | 2/2013 |
| WO | WO 2013/145409 A1 | 10/2013 |

OTHER PUBLICATIONS

International Search Report dated Oct. 18, 2016 issued in PCT/JP2016/071777.

*Primary Examiner* — Howard D Brown, Jr.
(74) *Attorney, Agent, or Firm* — Scully, Scott, Murphy & Presser, P.C.

(57) ABSTRACT

A disclosed image processing apparatus includes a processor comprising hardware, the processor being configured to obtain a plurality of temporally continuous images generated by continuously imaging a subject illuminated with illumination light; calculate a correction coefficient on the basis of a correction target frame among the plurality of images; revise the correction coefficient of the correction target frame on the basis of the correction coefficient of each of a plurality of frames within a predetermined time set beforehand from a shooting time of the correction target frame; and create a display image on the basis of the correction target frame and the correction coefficient.

20 Claims, 17 Drawing Sheets

(51) Int. Cl.
   *A61B 1/04*   (2006.01)
   *A61B 1/00*   (2006.01)
   *A61B 1/06*   (2006.01)
   *G06T 5/50*   (2006.01)

(52) U.S. Cl.
   CPC ............... *A61B 1/04* (2013.01); *A61B 1/063* (2013.01); *G06T 5/009* (2013.01); *G06T 5/50* (2013.01); *G06T 2207/10016* (2013.01); *G06T 2207/10024* (2013.01); *G06T 2207/10068* (2013.01); *G06T 2207/20182* (2013.01); *G06T 2207/20208* (2013.01); *G06T 2207/20216* (2013.01)

(58) Field of Classification Search
   CPC . G06T 2207/10068; G06T 2207/20182; G06T 2207/20208; G06T 2207/20216; A61B 1/00009; A61B 1/00045; A61B 1/04; A61B 1/063; A61B 1/000094
   See application file for complete search history.

(56) References Cited

U.S. PATENT DOCUMENTS

| | | | |
|---|---|---|---|
| 2013/0293693 A1 | 11/2013 | Igarashi et al. | |
| 2014/0193099 A1* | 7/2014 | Yoshikawa | G06T 7/337 |
| | | | 382/295 |
| 2016/0128545 A1* | 5/2016 | Morita | G02B 7/36 |
| | | | 600/109 |
| 2017/0302837 A1* | 10/2017 | Sakai | A61B 1/00009 |
| 2021/0390693 A1* | 12/2021 | Zhang | A61B 1/0005 |

* cited by examiner

IMAGE PROCESSING APPARATUS, IMAGE PROCESSING METHOD, AND NON-TRANSITORY COMPUTER READABLE RECORDING MEDIUM

CROSS-REFERENCE TO RELATED APPLICATION

This application is a continuation of International Application No. PCT/JP2016/071777, filed on Jul. 25, 2016, the entire contents of which are incorporated herein by reference.

BACKGROUND

The present invention relates to an image processing apparatus, an image processing method, and a non-transitory computer readable recording medium storing a program that causes the image processing apparatus to perform the image processing method.

Image signal generating technologies using an endoscope have been known, in which an image of a subject is captured by illuminating the subject with light having a predetermined wavelength band. For example, there is a correction process of enhancing a first image signal having a spectral characteristic in a narrow band in a hemoglobin light absorption of a living tissue, based on a difference between the first image signal and a second image signal having a spectral characteristic in which an absorption is lower than that of the first image signal (see WO 2013/145409 A).

SUMMARY

The present disclosure has been made in view of the above and is directed to an improvement in an image processing apparatus, an image processing method, and a non-transitory computer readable recording medium storing a program that causes the image processing apparatus to perform the image processing method According to a first aspect of the present disclosure, an image processing apparatus is provided which includes a processor comprising hardware, the processor being configured to obtain a plurality of images that are temporally continuous, the plurality of images being generated by continuously imaging a subject illuminated with illumination light; calculate a correction coefficient on the basis of a correction target frame among the plurality of images; revise the correction coefficient of the correction target frame on the basis of the correction coefficient of each of a plurality of frames within a predetermined time set beforehand from a shooting time of the correction target frame; and create a display image on the basis of the correction target frame and the correction coefficient.

According to a second aspect of the present disclosure, an image processing method to be executed by an image processing apparatus is provided. The method includes obtaining a plurality of images that are temporally continuous, the plurality of images being generated by continuously imaging a subject illuminated with illumination light; calculating a correction coefficient for correcting each of the plurality of images on the basis of a correction target frame among the plurality of images; revising the correction coefficient of the correction target frame on the basis of the correction coefficient of each of a plurality of frames within a predetermined time set beforehand from a shooting time of the correction target frame; and creating a display image on the basis of the correction target frame and the correction coefficient.

According to a third aspect of the present disclosure, a non-transitory computer readable recording medium storing a program that causes a computer to execute a process is provided. The process includes obtaining a plurality of images that are temporally continuous, the plurality of images being generated by continuously imaging a subject illuminated with illumination light; calculating a correction coefficient for correcting each of the plurality of images on the basis of a correction target frame among the plurality of images; revising the correction coefficient of the correction target frame on the basis of the correction coefficient of each of a plurality of frames within a predetermined time set beforehand from a shooting time of the correction target frame; and creating a display image on the basis of the correction target frame and the correction coefficient.

The above and other features, advantages and technical and industrial significance of this invention will be better understood by reading the following detailed description of presently preferred embodiments of the disclosure, when considered in connection with the accompanying drawings.

DETAILED DESCRIPTION OF THE PREFERRED EMBODIMENTS

Figure 1:
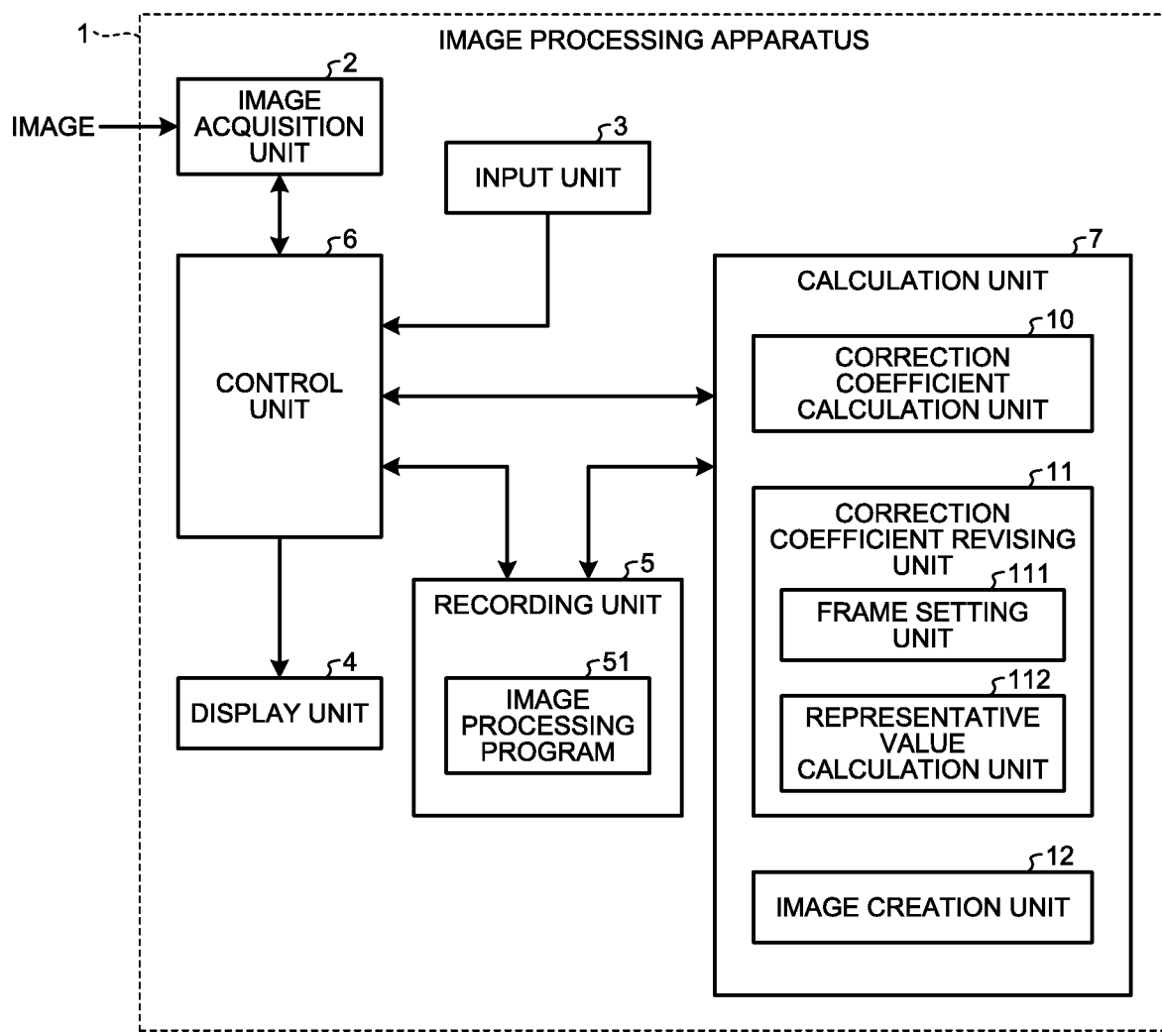
FIG. 1 is a block diagram illustrating a configuration of an image processing apparatus according to a first embodiment of the present disclosure.

Hereinafter, an image processing apparatus, an image processing method, and a program, according to embodiments of the present disclosure will be described with reference to the drawings. Note that the present disclosure is not limited by these embodiments. In the description of the drawings, the same portions are denoted by the same reference numerals.

First Embodiment

Configuration of Image Processing Apparatus

FIG. 1 is a block diagram illustrating a configuration of an image processing apparatus according to a first embodiment of the present disclosure. An image processing apparatus 1 according to the first embodiment, as an example, generates any of a display image that has enhanced tissues, mucosa, blood vessels, lesions, and the like, of a living body with respect to an intraluminal image group (moving image data of an intraluminal image) constituted with a plurality of temporally continuous intraluminal images obtained by continuously imaging the lumen of a living body irradiated with light of a predetermined wavelength band by using an endoscope (endoscope such as a flexible endoscope or a rigid endoscope) or a capsule endoscope (hereinafter simply referred to collectively as an "endoscope"); a display image with the image brightness corrected, a display image that has corrected blood vessels to facilitate observation with respect to the intraluminal image group; and a display image that has corrected a scattering substance to facilitate observation with respect to the intraluminal image group. The typical intraluminal image is a color image having a pixel level (pixel value) for wavelength components of R (red), G (green), and B (blue) at each of pixel positions.

The image processing apparatus 1 illustrated in FIG. 1 includes: an image acquisition unit 2, an input unit 3, a display unit 4, a recording unit 5, a control unit 6, and a calculation unit 7. The image acquisition unit 2 obtains, from an endoscope or outside, a time-series image (moving image data) constituted with image data (image signal) corresponding to an image captured by an endoscope and a plurality of temporally continuous images generated by continuously capturing a subject. The input unit 3 receives an input signal input by operation from outside. The display unit 4 displays images and various types of information. The recording unit 5 that records image data and moving image data obtained by the image acquisition unit 2, and various programs. The control unit 6 controls overall operation of the image processing apparatus 1. The calculation unit 7 performs predetermined image processing on an image or an intraluminal image group.

The image acquisition unit 2 is configured appropriately in accordance with system modes including an endoscope. For example, when a portable recording medium is used to transfer image data with an endoscope, the image acquisition unit 2 is configured as a reader device on which the recording medium is detachably attached and that reads recorded image data. Additionally, when a server is used to record image data captured by an endoscope, the image acquisition unit 2 is configured with a communication device, or the like, capable of two-way communications with the server and obtains image data by performing data communications with the server. Alternatively, the image acquisition unit 2 may be constituted of an interface device or the like, to which image data is input from the endoscope via a cable.

The input unit 3 is implemented with input devices such as a keyboard, a mouse, a touch panel, and various switches, and input signals received in response to the operation from outside to the control unit 6.

The display unit 4 is implemented by a display device such as a liquid crystal or an organic electro luminescence (EL) display panel, and displays various screens including an intraluminal image under the control of the control unit 6.

The recording unit 5 is implemented by various IC memories such as a flash memory, a read only memory (ROM), and a random access memory (RAM), and a hard disk or the like that is built-in or connected by a data communication terminal. The recording unit 5 records image data and moving image data obtained by the image acquisition unit 2, programs for operating the image processing apparatus 1 and for causing the image processing apparatus 1 to execute various functions, data to be used during execution of this program, or the like. For example, the recording unit 5 records an image processing program 51 that generates an enhanced image in which tissues, mucosa, blood vessels, lesions, or the like in a living body are enhanced with respect to the intraluminal image group, and records various types of information or the like used during execution of the program.

The control unit 6 is implemented by a central processing unit (CPU). The control unit 6 integrally controls general operation of the image processing apparatus 1. Specifically, the control unit 6 reads various programs recorded in the recording unit 5, thereby transmitting instructions and data to individual components of the image processing apparatus 1 in accordance with image data input from the image acquisition unit 2, input signals input from the input unit 3, or the like.

The calculation unit 7 is implemented by a CPU or the like. The calculation unit 7 reads the image processing program 51 recorded in the recording unit 5 and executes image processing of generating a display image that has enhanced tissues, mucosa, blood vessels, and lesions (hereinafter referred to as a "specific site") in the living body with respect to the image group.

Detailed Configuration of Calculation Unit

Next, a detailed configuration of the calculation unit 7 will be described.

The calculation unit 7 includes a correction coefficient calculation unit 10, a correction coefficient revising unit 11, and an image creation unit 12.

The correction coefficient calculation unit 10 calculates correction coefficients for correcting each of a plurality of images on the basis of an image of a correction target frame, among a plurality of images obtained by the image acquisition unit 2.

The correction coefficient revising unit 11 revises the correction coefficient of the correction target frame on the basis of a plurality of correction coefficients of each of a plurality of frames (hereinafter referred to as "time-series vicinity frames") within a predetermined time set beforehand from the shooting time of the image of the correction target frame. The correction coefficient revising unit 11 includes a frame setting unit 111 and a representative value calculation unit 112.

The frame setting unit 111 sets a time-series vicinity frame used for setting the representative value.

The representative value calculation unit 112 calculates a representative value on the basis of the correction coefficient of the correction target frame and the correction coefficient of the time-series vicinity frame set by the frame setting unit 111.

The image creation unit 12 creates a display image on the basis of the image and the correction coefficient of the correction target frame and records the created corrected image in the recording unit 5 or outputs the image to the display unit 4 via the control unit 6.

Processing in Image Processing Apparatus

Figure 2:
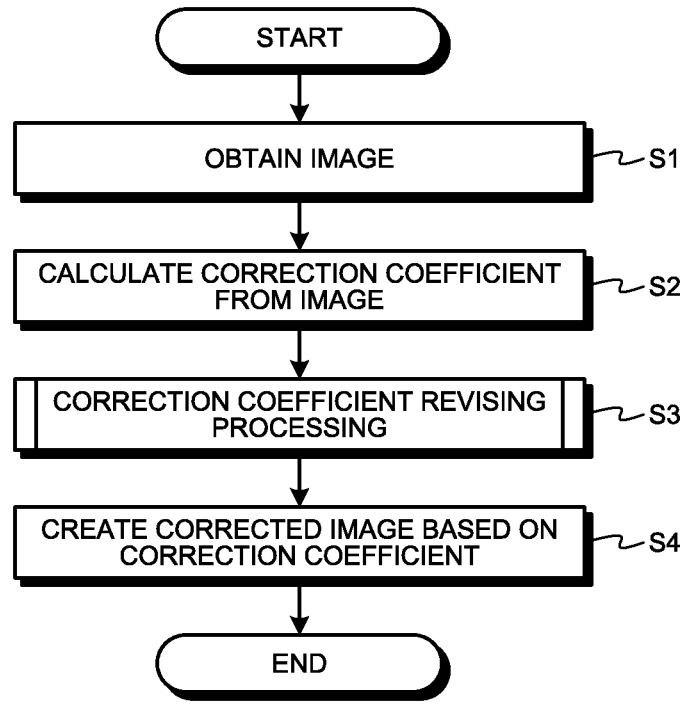
FIG. 2 is a flowchart illustrating an outline of image processing executed by the image processing apparatus according to the first embodiment of the present disclosure.

Next, an image processing method executed by the image processing apparatus 1 will be described. FIG. 2 is a flowchart illustrating a process executed by the image processing apparatus 1.

As illustrated in FIG. 2, the image acquisition unit 2 first obtains an image, which captured by an endoscope or the like, from the outside, and outputs the obtained image to the recording unit 5, which in turn records the image (Step S1). Here, the image includes an intraluminal image obtained by imaging any of a gastrointestinal tract, a blood vessel, and an organ. In addition, the illumination light used in the imaging of the intraluminal image is any of natural light, illumination light from a light emitting diode (LED) light source, illumination light from a laser light source, or illumination light from a halogen lamp. Furthermore, the illumination light used in the imaging of the intraluminal image may be illumination light having an intentionally limited predetermined wavelength band. Specifically, the illumination light may have a wavelength band in the vicinity of 770 nm, a wavelength band from 395 nm to 445 nm, a wavelength band from 530 nm to 550 nm, a wavelength band from 585 nm to 615 nm, or a wavelength band of 610 nm to 730 nm.

Subsequently, the correction coefficient calculation unit 10 calculates a correction coefficient from the image (Step S2). Specifically, the correction coefficient calculation unit 10 calculates a correction coefficient to be used for correcting the brightness of an image, enhancing a specific site, correcting so as to facilitate observation of a blood vessel, or correcting so as to facilitate observation of a scattering substance. For example, when a blood vessel is extracted at a specific depth on the basis of a plurality of images and the extracted blood vessel is combined to a certain image, an example of the correction coefficient would be blood vessel information associated with the blood vessel to be combined to the image.

Thereafter, the correction coefficient revising unit 11 executes correction coefficient revising processing of calculating a representative value on the basis of the correction coefficients of the correction target frame and a plurality of frames of time-series vicinity frames, and then revising the calculated representative value so as to be the correction coefficient (Step S3).

Figure 3:
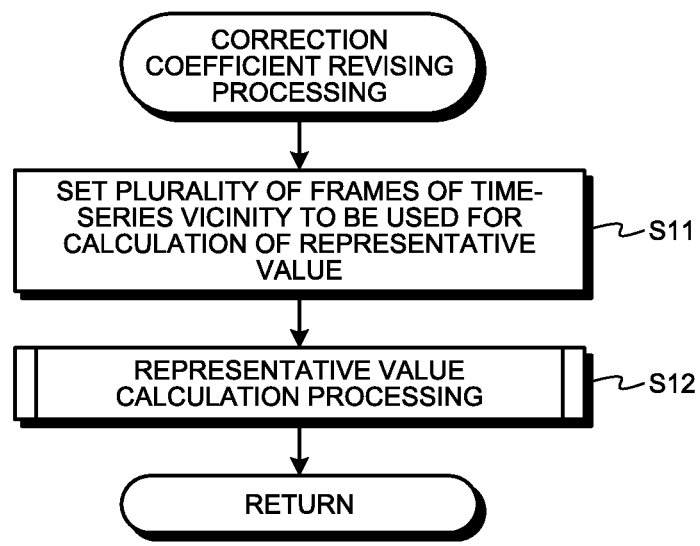
FIG. 3 is a flowchart illustrating an outline of correction coefficient revising processing in FIG. 2.

FIG. 3 is a flowchart illustrating an outline of correction coefficient revising processing of Step S3 in FIG. 2. As illustrated in FIG. 3, the frame setting unit 111 sets a plurality of time-series vicinity frames to be used for calculating a representative value (Step S11). For example, the frame setting unit 111 may set an image of one or more preceding frames acquired in time series (earlier in shooting time) before the shooting time of the image of the correction target frame, where the one or more preceding frames excludes the correction target frame, as a plurality of time-series vicinity frames to be used for calculating the representative value. Alternatively, the frame setting unit 111 may set an image of one or more succeeding frames acquired in time series (later in shooting time) after the shooting time of the image of the correction target frame, where the one or more preceding frames excludes the correction target frame, as a plurality of time-series vicinity frames to be used for calculating the representative value. Note that the frame setting unit 111 may include the correction target frame in the plurality of time-series vicinity frames to be used for calculating the representative value.

Subsequently, the representative value calculation unit 112 executes representative value calculation processing of calculating a representative value from the information based on the correction coefficient of the correction target frame and the correction coefficient in the time-series vicinity frame, and then revising the correction coefficient of the correction target frame (Step S12). After Step S12, the process returns to the main routine in FIG. 2.

Figure 4:
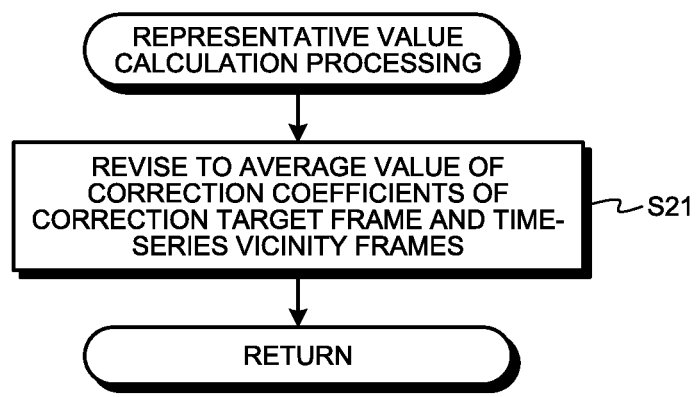
FIG. 4 is a flowchart illustrating an outline of representative value calculation processing in FIG. 3.

FIG. 4 is a flowchart illustrating an outline of representative value calculation processing in Step S12 in FIG. 3. As illustrated in FIG. 4, the representative value calculation unit 112 revises the correction coefficient of the correction target frame to an average value of the correction coefficient of the correction target frame and the correction coefficient of the time-series vicinity frame (Step S21).

Figure 5:
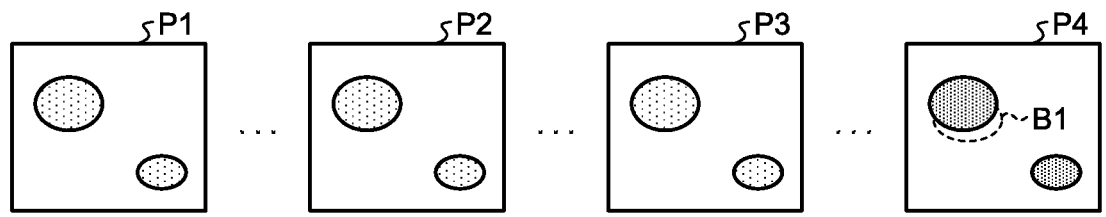
FIG. 5 is a diagram schematically illustrating an example of a conventional time-series image.

When images reflecting the correction result are displayed as a moving image in a case where the correction coefficient is extremely changed between frames, blurring would arise in the image, making the image less easy to observe for the user. More specifically, as illustrated in FIG. 5, when it is assumed that time-series vicinity frames P1, P2, P3, and P4 exist at times t-3, t-2, t-1 and t, respectively, and correction coefficients of images P1, P2, P3, and P4 are $K\_t-3$, $K\_t-2$, $K\_t-1$, and $K\_t$, respectively, a specific site B1 of an image P4 is blurred (broken line portion) because the correction coefficients $K\_t-3$ to $K\_t$ change greatly in time series.

Figure 6:
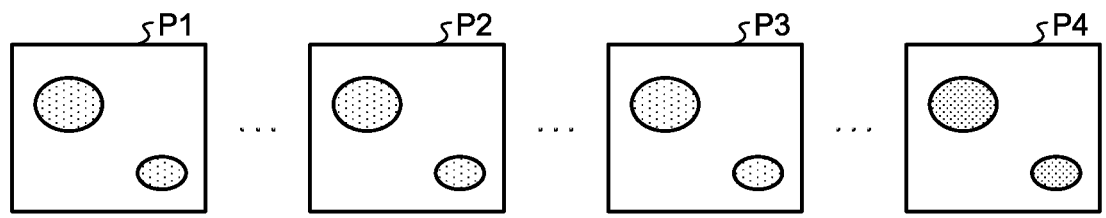
FIG. 6 is a diagram schematically illustrating an example of a time-series image after image processing by the image processing apparatus according to the first embodiment of the present disclosure.
Figure 7:
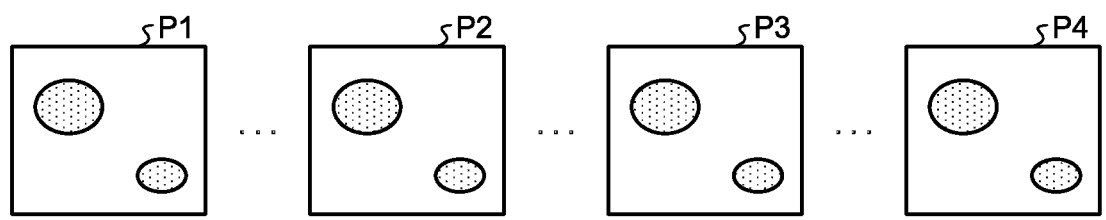
FIG. 7 is a diagram schematically illustrating another example of a time-series image after image processing by the image processing apparatus according to the first embodiment of the present disclosure.

In contrast to this, the representative value calculation unit 112 according to the first embodiment revises the correction coefficient of the correction target frame to the average value of the correction coefficient of the correction target frame and each of the correction coefficients of the time-series vicinity frames. This can decrease the change in the correction coefficient between the frames, leading to suppression of blurring. More specifically, as illustrated in FIG. 6, when it is assumed that the time-series vicinity frames P1, P2, P3, and P4 exist at times t-3, t-2, t-1 and t, respectively, and correction coefficients of images P1, P2, P3, and P4 are $K\_t-3$, $K\_t-2$, $K\_t-1$, and $K\_t$, respectively, the representative value calculation unit 112 revises the correction coefficient of the correction target frame to an average value $(((K\_t-3)+(K\_t-2)+(K\_t-1)+(K\_t))/4)$. With this processing, the correction coefficient would not change in time series, making it possible to suppress the blurring. Furthermore, as illustrated in FIG. 7, when the time-series vicinity frames P1 to P3 exist at times of t-3 to t-1, respectively, the representative value calculation unit 112 may revise the correction coefficient of the correction target frame to an average value $(((K\_t-3)+(K\_t-2)+(K\_t-1))/3)$ of the correction coefficients of the time-series vicinity frames. With this processing, blurring can be prevented.

Furthermore, in calculating the average value, the representative value calculation unit 112 may first align inter-frame pixel positions and may thereafter calculate the average value of the correction coefficient of the correction target frame and each of correction coefficients of the time-series vicinity frames. Note that while the representative value calculation unit 112 calculates the average value of the correction coefficient of the correction target frame and each of the correction coefficients of the time-series vicinity frames as the representative value, and revises the correction coefficient of the correction target frame to the obtained representative value, the calculation method may be changed depending on a type of the subject of the target image. For example, a median or the like may be calculated instead of the average value. After Step S21, the process returns to the correction coefficient revising processing of FIG. 3.

Returning to FIG. 2, Step S4 and subsequent processing will be described.

In Step S4, the image creation unit 12 creates a corrected image based on the correction coefficient. Specifically, the image creation unit 12 creates a corrected image based on the image of the correction target frame and the correction coefficient. After Step S4, the process is terminated.

According to the first embodiment of the present disclosure described above, it is possible to suppress blurring of an image.

Modification of First Embodiment

Next, a modification of the first embodiment of the present disclosure will be described. The modification according to the first embodiment has a different representative value calculation processing executed by the image processing apparatus. Hereinafter, representative value calculation processing executed by the image processing apparatus according to a modification of the first embodiment will be described. A same reference sign will be given to the configuration identical to the configuration of the image processing apparatus 1 according to the above-described first embodiment, and description for this will be omitted.

Figure 8:
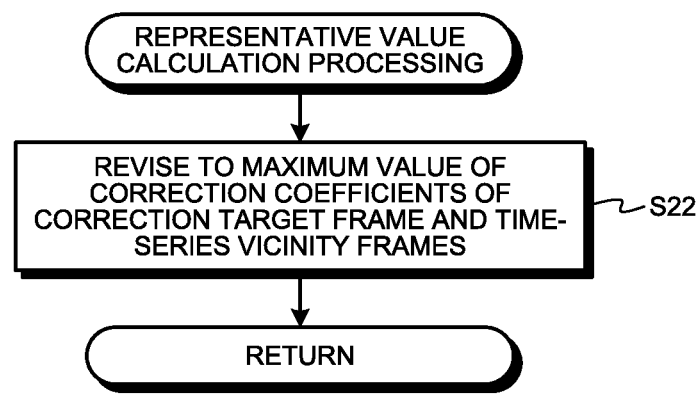
FIG. 8 is a flowchart illustrating an outline of representative value calculation processing executed by an image processing apparatus according to a modification of the first embodiment of the present disclosure.

FIG. 8 is a flowchart illustrating an outline of representative value calculation processing executed by the image processing apparatus according to a modification of the first embodiment. As illustrated in FIG. 8, the representative value calculation unit 112 revises the correction coefficient of the correction target frame to a maximum value of the correction coefficient of the correction target frame and the correction coefficient of the time-series vicinity frame (Step S22). When images reflecting the correction result are displayed as a moving image in a case where the correction coefficient varies between the frames, flickering would arise in the image, making the image less easy to observe for the user (refer to above-described FIG. 5). In contrast, the representative value calculation unit 112 according to the modification of the first embodiment revises the correction coefficient of the correction target frame to the maximum value in each of the correction coefficients of the correction target frame and the time-series vicinity frames. This suppresses the change in the correction coefficient even when the frame changes (because similar images can be output), making it possible to reduce the flickering of the image (refer to FIG. 6 described above). Note that similarly to the above-described first embodiment, in calculating the maximum value, the representative value calculation unit 112 may first align inter-frame pixel positions and may thereafter calculate the maximum value of the correction coefficient of the correction target frame and the correction coefficient of each of the time-series vicinity frames. Note that while the representative value calculation unit 112 calculates the maximum value of the correction coefficient of the correction target frame and the correction coefficient of each of the time-series vicinity frames as the representative value, and revises the correction coefficient of the correction target frame to the obtained representative value, the calculation method may be changed depending on a type of the subject of the target image. For example, a minimum value or the like may be calculated. After Step S22, the process returns to the correction coefficient revising processing of FIG. 3.

According to the modification of the first embodiment of the present disclosure described above, it is possible to suppress blurring of the time-series image group.

Second Embodiment

Next, a second embodiment of the present disclosure will be described. An image processing apparatus according to the second embodiment is different in configuration from the image processing apparatus 1 according to the above-described first embodiment. Hereinafter, the configuration of the image processing apparatus according to the second embodiment will be first described and thereafter an image processing method executed by the image processing apparatus according to the second embodiment will be described. A same reference sign will be given to the configuration identical to the configuration of the image processing apparatus 1 according to the above-described first embodiment, and description for this will be omitted.

Configuration of Image Processing Apparatus

Figure 9:
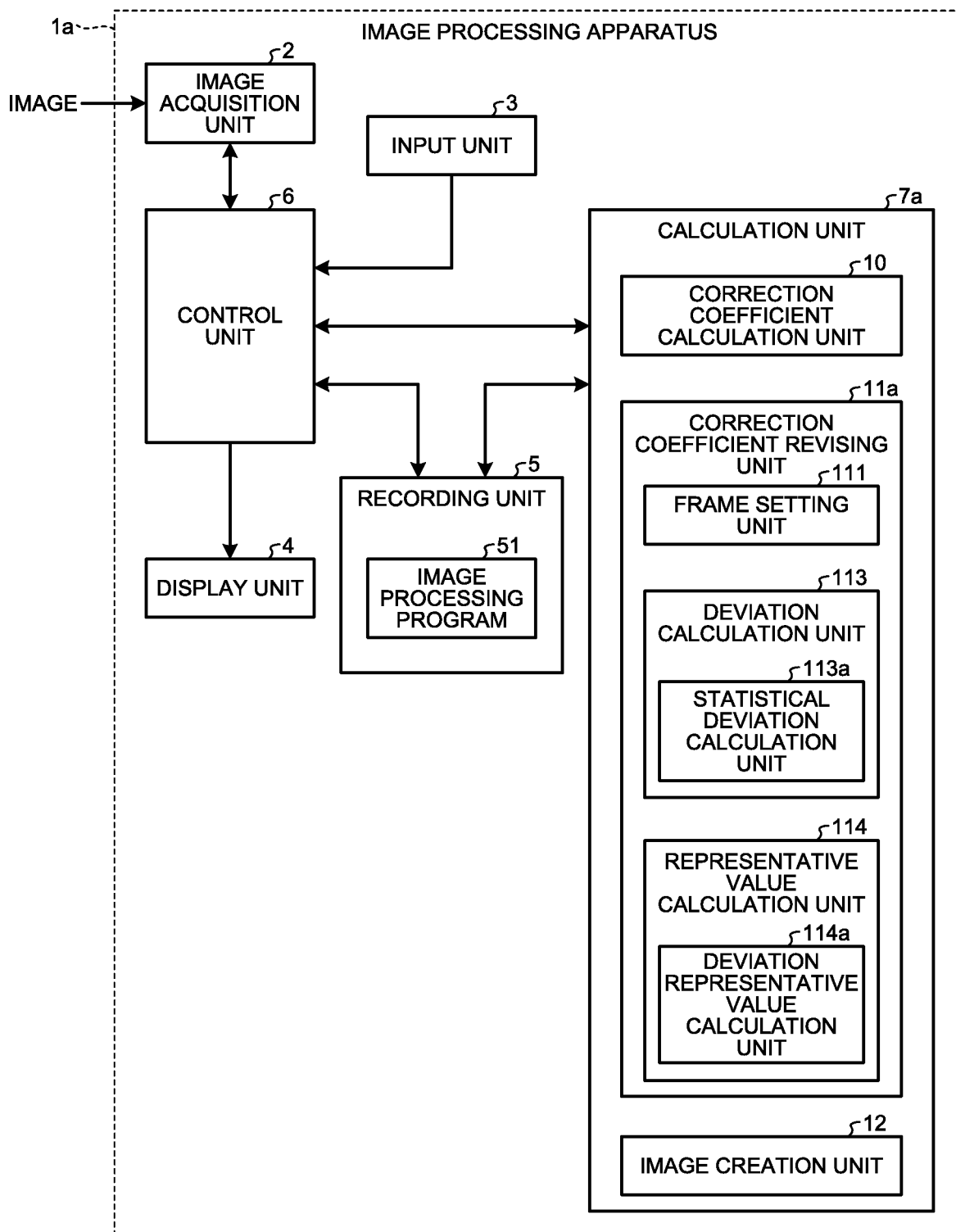
FIG. 9 is a block diagram illustrating a configuration of an image processing apparatus according to a second embodiment of the present disclosure.

FIG. 9 is a block diagram illustrating a configuration of an image processing apparatus according to the second embodiment of the present disclosure. An image processing apparatus 1a illustrated in FIG. 9 includes a calculation unit 7a in place of the calculation unit 7 of the image processing apparatus 1 according to the above-described first embodiment.

The calculation unit 7a is implemented by a CPU or the like. The calculation unit 7a reads the image processing program 51 recorded in the recording unit 5 and executes image processing of generating a display image on the basis of an image group.

Detailed Configuration of Calculation Unit

Next, a detailed configuration of the calculation unit 7a will be described.

The calculation unit 7a includes a correction coefficient revising unit 11a in place of the correction coefficient revising unit 11 of the calculation unit 7 according to the above-described first embodiment.

The correction coefficient revising unit 11a includes a frame setting unit 111, a deviation calculation unit 113, and a representative value calculation unit 114.

The deviation calculation unit 113 calculates deviation of a correction coefficient of a correction target frame or a correction coefficient of one or more frames in a time-series vicinity frame, with respect to a correction coefficient in a frame within a specific time-series section. The deviation calculation unit 113 also includes a statistical deviation calculation unit 113a that calculates deviation with respect to the correction coefficient in the frames in a specific time-series section from a distribution state based on the correction coefficient of each of the time-series vicinity frames.

The representative value calculation unit 114 calculates a representative value on the basis of the correction coefficient of the correction target frame and the correction coefficient of one or more frames set by the frame setting unit 111. Furthermore, the representative value calculation unit 114 includes a deviation representative value calculation unit 114a that calculates a representative value of correction coefficient of the correction target frame on the basis of the deviation.

Processing in Image Processing Apparatus

Figure 10:
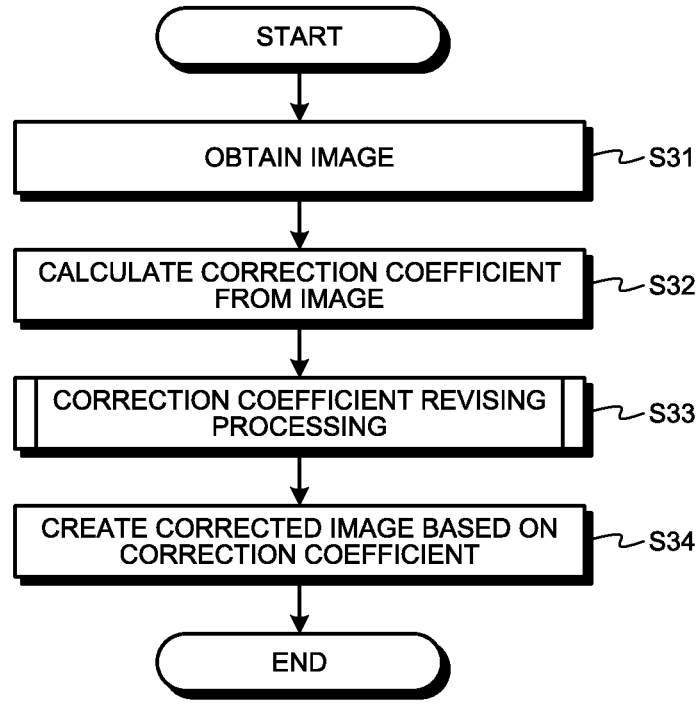
FIG. 10 is a flowchart illustrating an outline of image processing executed by the image processing apparatus according to the second embodiment of the present disclosure.

Next, an image processing method executed by the image processing apparatus 1a will be described. FIG. 10 is a flowchart illustrating an outline of processing executed by the image processing apparatus 1a. In FIG. 10, Steps S31, S32, and S34 respectively correspond to the above-described Steps S1, S2, and S4 of FIG. 2 described above, and thus, description will be omitted.

In Step S33, the correction coefficient revising unit 11a calculates a representative value on the basis of the correction coefficients of the time-series vicinity frames in the correction target frame, and executes correction coefficient revising processing of revising the correction coefficient to the calculated representative value. After Step S33, the image processing apparatus 1a advances the process to Step S34.

Figure 11:
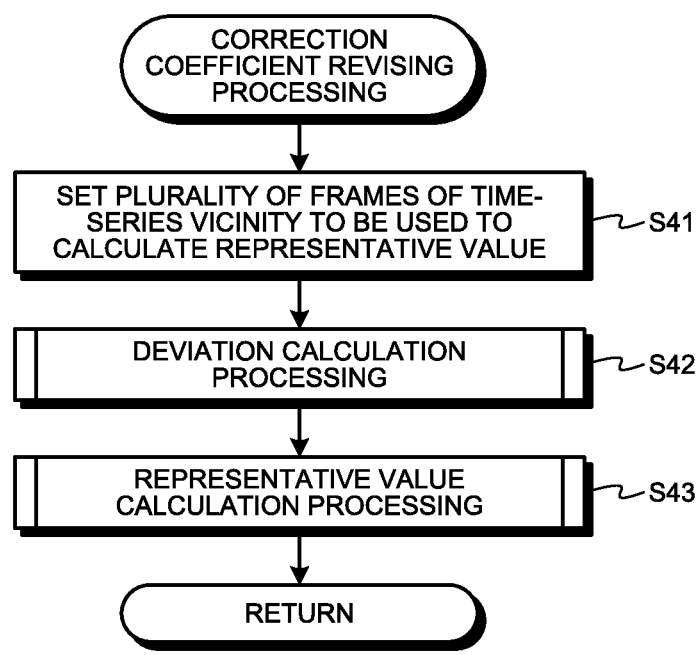
FIG. 11 is a flowchart illustrating an outline of correction coefficient revising processing in FIG. 10.

FIG. 11 is a flowchart illustrating an outline of correction coefficient revising processing in Step S33 in FIG. 10. In FIG. 11, since Step S41 is similar to Step S11 in FIG. 3 described above, its description will be omitted.

In Step S42, the deviation calculation unit 113 executes deviation calculation processing of calculating deviation of the correction coefficient of the correction target frame or the correction coefficient of one or more frames in the time-series vicinity frames, with respect to the correction coefficient in the frame in a specific time-series section. As a method of setting a frame in a specific time-series section, a time-series vicinity frame may be set as a frame in the specific time-series section. Furthermore, as a calculation method implemented by the deviation calculation unit 113, for example, a difference may be calculated between the correction coefficient of a frame in a time-series section and the correction coefficient of the correction target frame as the deviation. Alternatively, a difference may be calculated between the correction coefficient of the frame in a time-series section and the correction coefficient of one or more frames in the time-series vicinity frames as the deviation. After Step S42, the image processing apparatus 1a advances the process to Step S43 described below.

Figure 12:
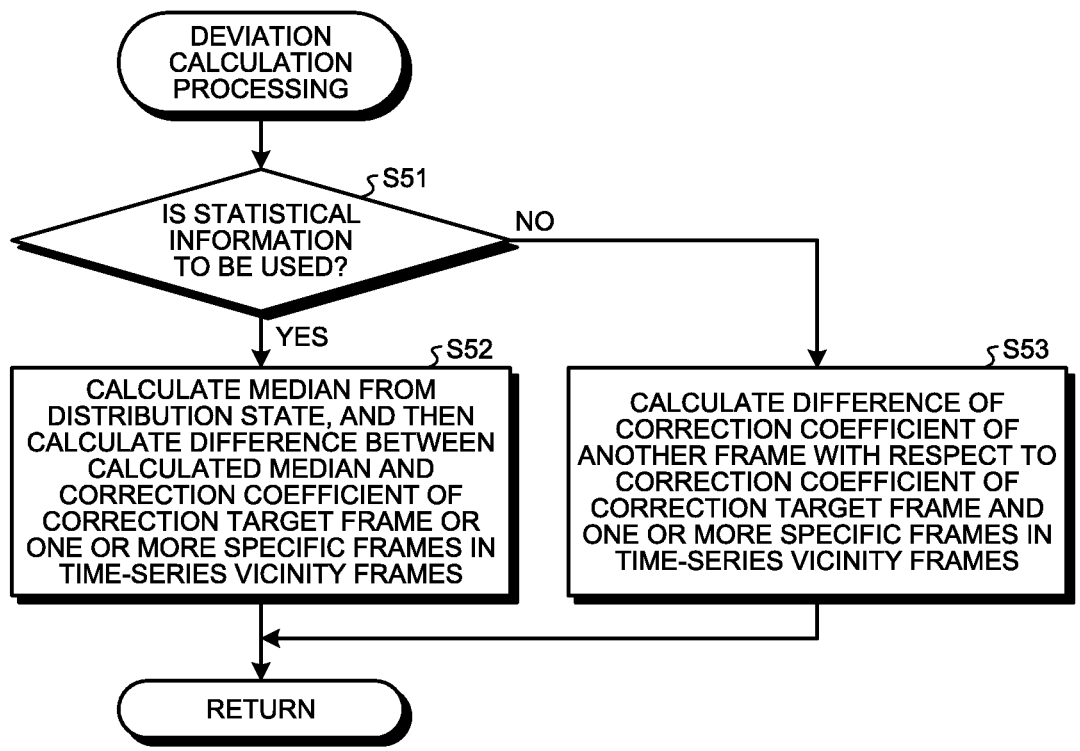
FIG. 12 is a flowchart illustrating an outline of deviation calculation processing in FIG. 11.

FIG. 12 is a flowchart illustrating an outline of deviation calculation processing in Step S42 in FIG. 11. As illustrated in FIG. 12, when the image processing apparatus 1a uses statistical information (Step S51: Yes), the image processing apparatus 1a advances the process to Step S52 described below. In contrast, when the image processing apparatus 1a does not use the statistical information (Step S51: No), the image processing apparatus 1a advances the process to Step S53 described below. Note that the calculation unit 7a judges whether to use the statistical information in accordance with the setting corresponding to the instruction signal input by the user operating the input unit 3. Note that the calculation unit 7a may be configured to automatically judge whether to use the statistical information depending on the magnitude relation of the correction coefficient.

In Step S52, the statistical deviation calculation unit 113a calculates a median from the distribution state of the correction coefficients in the frames in the time-series section, and calculates a difference between the calculated median and the correction coefficient of the correction target frame or the correction coefficient of one or more specific frames in the time-series vicinity frames. This processing calculates deviation of the correction target frame or the deviation of one or more specific frames in the time-series vicinity frame, leading to calculation of one or more deviations. After Step S52, the process returns to the correction coefficient revising processing of FIG. 11.

In Step S53, the deviation calculation unit 113 calculates difference between the correction coefficient of a specific frame in the time-series section and the correction coefficient of the correction target frame or the correction coefficient of a specific frame in the time-series vicinity frame. In this case, when plural specific frames exist in the time-series section, the deviation calculation unit 113 may calculate a difference between the correction coefficient of each of the plurality of specific frames and the correction coefficient of the correction target frame or the correction coefficient of the specific frame in the time-series vicinity frame, and may calculate a sum of the calculated differences as the deviation. This processing calculates deviation of the correction target frame or the deviation of one or more specific frames in the time-series vicinity frame, leading to calculation of one or more deviations. Note that the deviation calculation unit 113 may calculate an average value of the differences in place of the sum of the differences between the correction coefficient of each of the plurality of specific frames and the correction coefficient of the correction target frame or the correction coefficient of the specific frame in the time-series vicinity frames. Furthermore, similarly to the first embodiment described above, the deviation calculation unit 113 may perform the calculation in units of pixels after performing pixel alignment, specifically, may perform the calculation in units of pixels by using an average value or the like of the correction coefficients of individual pixels in the entire image. After Step S53, the process returns to the correction coefficient revising processing of FIG. 11.

Returning to FIG. 11, Step S43 and subsequent processing will be described.

In Step S43, the representative value calculation unit 114 calculates a representative value by using information on the basis of the deviation, the correction coefficient of the correction target frame, and the correction coefficients of the time-series vicinity frames. After Step S43, the process returns to the main routine in FIG. 10.

Figure 13:
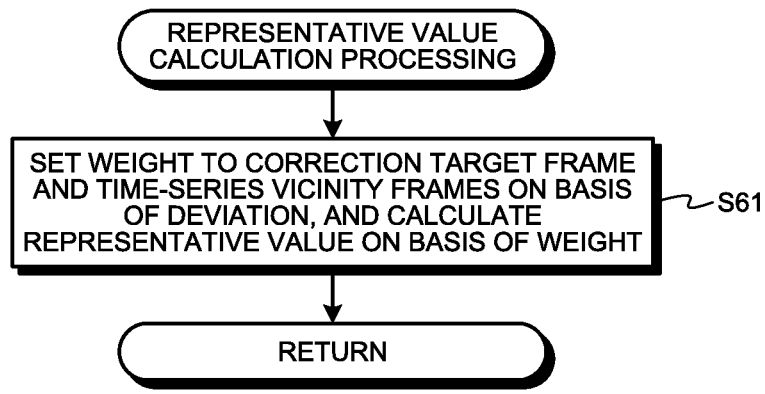
FIG. 13 is a flowchart illustrating an outline of representative value calculation processing in FIG. 11.

FIG. 13 is a flowchart illustrating an outline of representative value calculation processing in Step S43 in FIG. 11. As illustrated in FIG. 13, the deviation representative value calculation unit 114a sets the weight to the correction coefficient of the correction target frame and the correction coefficient of each of the time-series vicinity frames on the basis of the deviation, and calculates the representative value on the basis of the weight (Step S61). Specifically, the deviation representative value calculation unit 114a performs setting such that the greater the deviation is, the smaller the value of the weight becomes. For example, the deviation representative value calculation unit 114a sets the value of the weight with reference to a table beforehand that has been set such that the greater the difference between the deviation and the value of the correction coefficient is, the smaller the value of the weight becomes. Thereafter, the deviation representative value calculation unit 114a multiplies the weight of the correction coefficient in each of the frames by the correction coefficient, and then calculates an average value of the correction coefficients of individual frames after multiplication, as a representative value. After Step S61, the process returns to the correction coefficient revising processing of FIG. 11.

According to the second embodiment of the present disclosure described above, it is possible to suppress blurring of the time-series image group.

First Modification of Second Embodiment

Next, a first modification of the second embodiment of the present disclosure will be described. The first modification of the second embodiment has a different deviation calculation processing executed by the image processing apparatus. Hereinafter, the deviation calculation processing executed by the image processing apparatus according to the first modification of the second embodiment will be described. A same reference sign will be given to the configuration identical to the configuration of the image processing apparatus 1a according to the above-described second embodiment, and description of this will be omitted.

Figure 14:
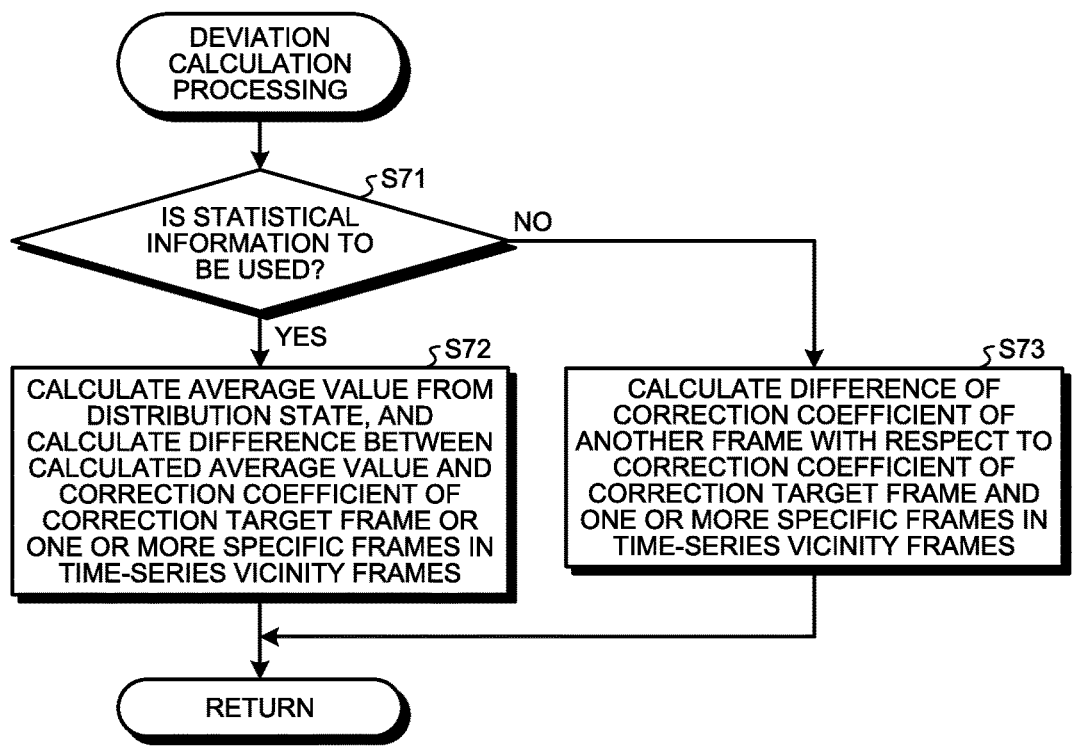
FIG. 14 is a flowchart illustrating an outline of deviation calculation processing executed by an image processing apparatus according to a first modification of the second embodiment of the present disclosure.

FIG. 14 is a flowchart illustrating an outline of deviation calculation processing executed by the image processing apparatus 1a according to the first modification of the second embodiment. Steps S71 and S73 in FIG. 14 correspond to Steps S51 and S53 in above-described FIG. 12, respectively, and thus, description for these will be omitted.

In Step S72, the statistical deviation calculation unit 113a calculates an average value from the distribution state of the correction coefficients in the frame in the time-series section, and calculates a difference between the calculated average value and the correction coefficient of the correction target frame or the correction coefficient of one or more specific frames in the time-series vicinity frames. This processing calculates deviation of the correction target frame or the deviation of one or more specific frames in the time-series vicinity frame, leading to calculation of one or more deviations. After Step S72, the process returns to the correction coefficient revising processing of FIG. 11.

According to the first modification of the second embodiment of the present disclosure described above, it is possible to suppress blurring of the time-series image group.

Second Modification of Second Embodiment

Next, a second modification of the second embodiment of the present disclosure will be described. The second modification of the second embodiment has a different deviation calculation processing executed by the image processing apparatus. Hereinafter, the deviation calculation processing executed by the image processing apparatus according to the second modification of the second embodiment will be described. A same reference sign will be given to the configuration identical to the configuration of the image processing apparatus 1a according to the above-described second embodiment, and description of this will be omitted.

Figure 15:
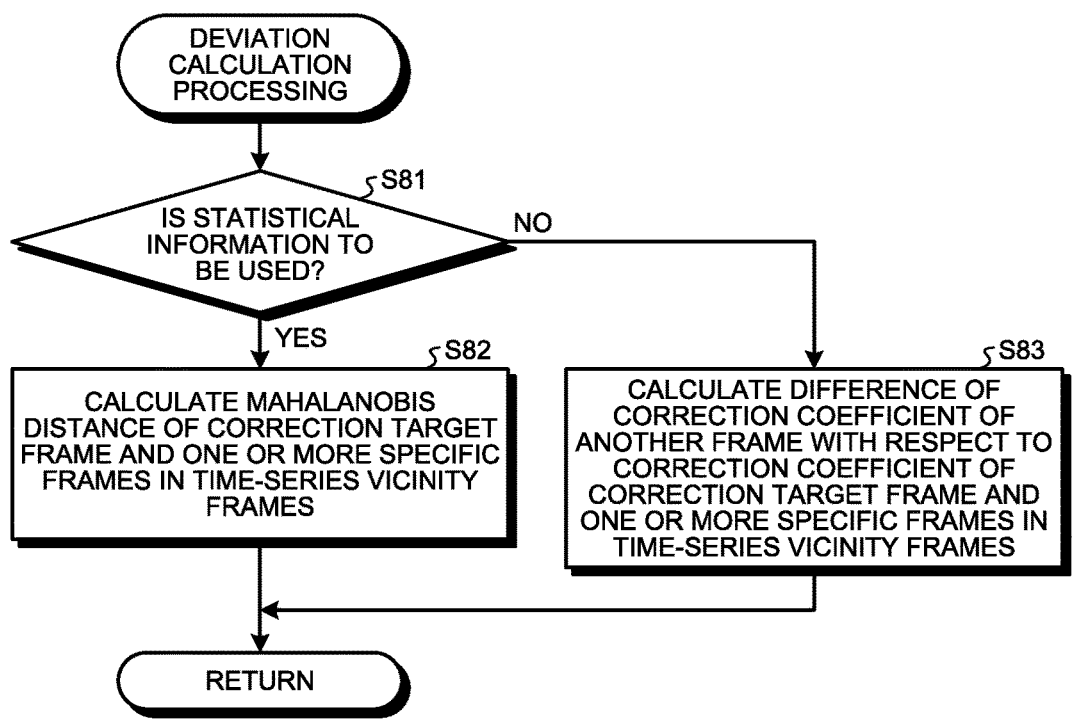
FIG. 15 is a flowchart illustrating an outline of deviation calculation processing executed by an image processing apparatus according to a second modification of the second embodiment of the present disclosure.

FIG. 15 is a flowchart illustrating an outline of the deviation calculation processing executed by the image processing apparatus according to the second modification of the second embodiment. Steps S81 and S83 in FIG. 15 correspond to Steps S51 and S53 in above-described FIG. 12, respectively, and thus, description for these will be omitted.

In Step S82, the Mahalanobis distance is calculated from the distribution state of the correction coefficients in the frames in the time-series section. With this processing, deviation of the correction target frame or the deviation of one or more specific frames in the time-series vicinity frames is calculated, leading to calculation of one or more deviations. After Step S82, the image processing apparatus 1a returns to the correction coefficient revising processing of FIG. 11.

According to the second modification of the second embodiment of the present disclosure described above, it is possible to suppress blurring of the time-series image group.

Third Modification of Second Embodiment

Next, a third modification of the second embodiment of the present disclosure will be described. The third modification of the second embodiment has a different representative value calculation processing executed by the image processing apparatus. Hereinafter, representative value calculation processing executed by the image processing apparatus according to the third modification of the second embodiment will be described. A same reference sign will be given to the configuration identical to the configuration of the image processing apparatus 1a according to the above-described second embodiment, and description of this will be omitted.

Figure 16:
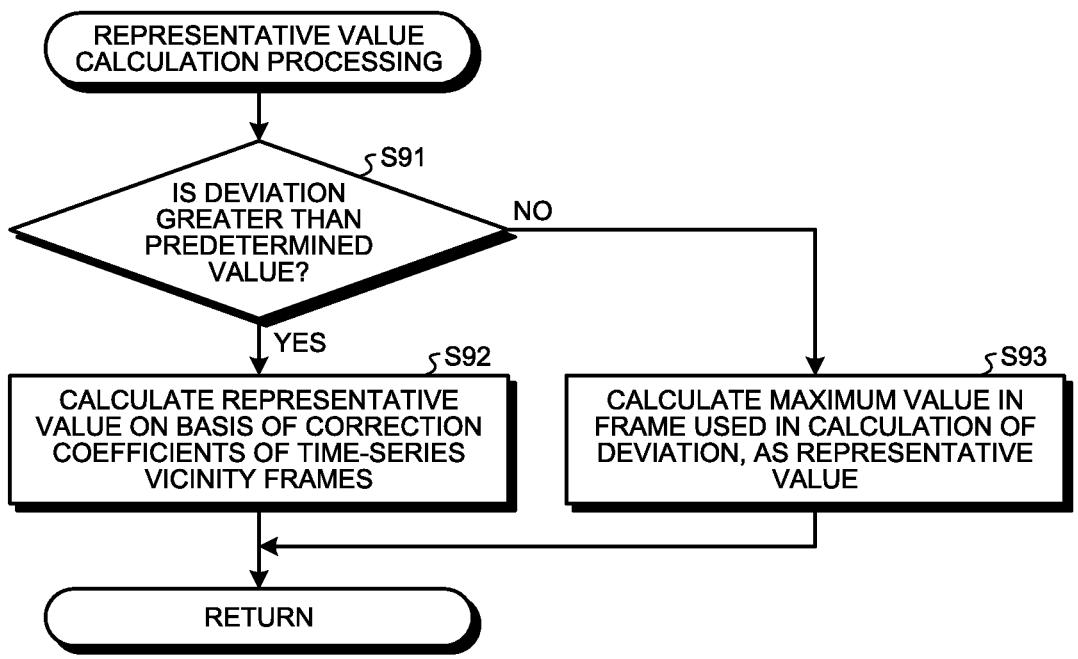
FIG. 16 is a flowchart illustrating an outline of representative value calculation processing executed by an image processing apparatus according to a third modification of the second embodiment of the present disclosure.

FIG. 16 is a flowchart illustrating an outline of representative value calculation processing executed by the image processing apparatus according to the third modification of the second embodiment.

As illustrated in FIG. 16, the control unit 6 judges whether the deviation calculated by the deviation calculation unit 113 is greater than a predetermined value (Step S91). When the control unit 6 judges that the deviation calculated by the deviation calculation unit 113 is greater than a predetermined value (Step S91: Yes), the image processing apparatus 1a advances the process to Step S92 described below. In contrast, when the control unit 6 judges that the deviation calculated by the deviation calculation unit 113 is not greater than the predetermined value (Step S91: No), the image processing apparatus 1a advances the process to Step S93 described below.

In Step S92, the representative value calculation unit 114 calculates a representative value on the basis of the correction coefficients of the time-series vicinity frames. Specifically, when the deviation is greater than a predetermined value in the case of using the deviation of the correction target frame alone, because the correction coefficient of the correction target frame is away from the median, the reliability of the correction coefficient of the correction target frame can be taken into consideration. Therefore, the representative value calculation unit 114 calculates a representative value on the basis of the correction coefficients of the time-series vicinity frames. For example, similarly to the case of FIG. 13 described above, weights are set for the correction coefficient of the correction target frame and each of the correction coefficients of the time-series vicinity frames on the basis of the deviation, and the weights of the correction coefficients and the correction coefficients are multiplied to each other, and thereafter, an average value of correction coefficients of individual frames after multiplication is calculated as a representative value. After Step S92, the process returns to the correction coefficient revising processing of FIG. 11.

In Step S93, the representative value calculation unit 114 calculates the maximum value in the frame used for calculating the deviation, as a representative value. Specifically, when the deviation is not greater than a predetermined value, a large change would not occur in the correction coefficient. Therefore, the representative value calculation unit 114 calculates, as a representative value, the correction coefficient of the maximum value out of the correction coefficient of the correction target frame and the correction coefficients of the time-series vicinity frames. It is possible to reduce the flickering for each of frames with the use of the maximum value rather than adapting the correction coefficient for each of the frames.

According to the third modification of the second embodiment of the present disclosure described above, it is possible to suppress blurring of the time-series image group.

Third Embodiment

Next, a third embodiment of the present disclosure will be described. An image processing apparatus according to the third embodiment is different in configuration from the image processing apparatus 1 according to the above-described first embodiment. Hereinafter, the configuration of the image processing apparatus according to the third embodiment will be first described and thereafter an image processing method executed by the image processing apparatus according to the third embodiment will be described. A same reference sign will be given to the configuration identical to the configuration of the image processing apparatus 1 according to the above-described first embodiment, and description for this will be omitted.

Configuration of Image Processing Apparatus

Figure 17:
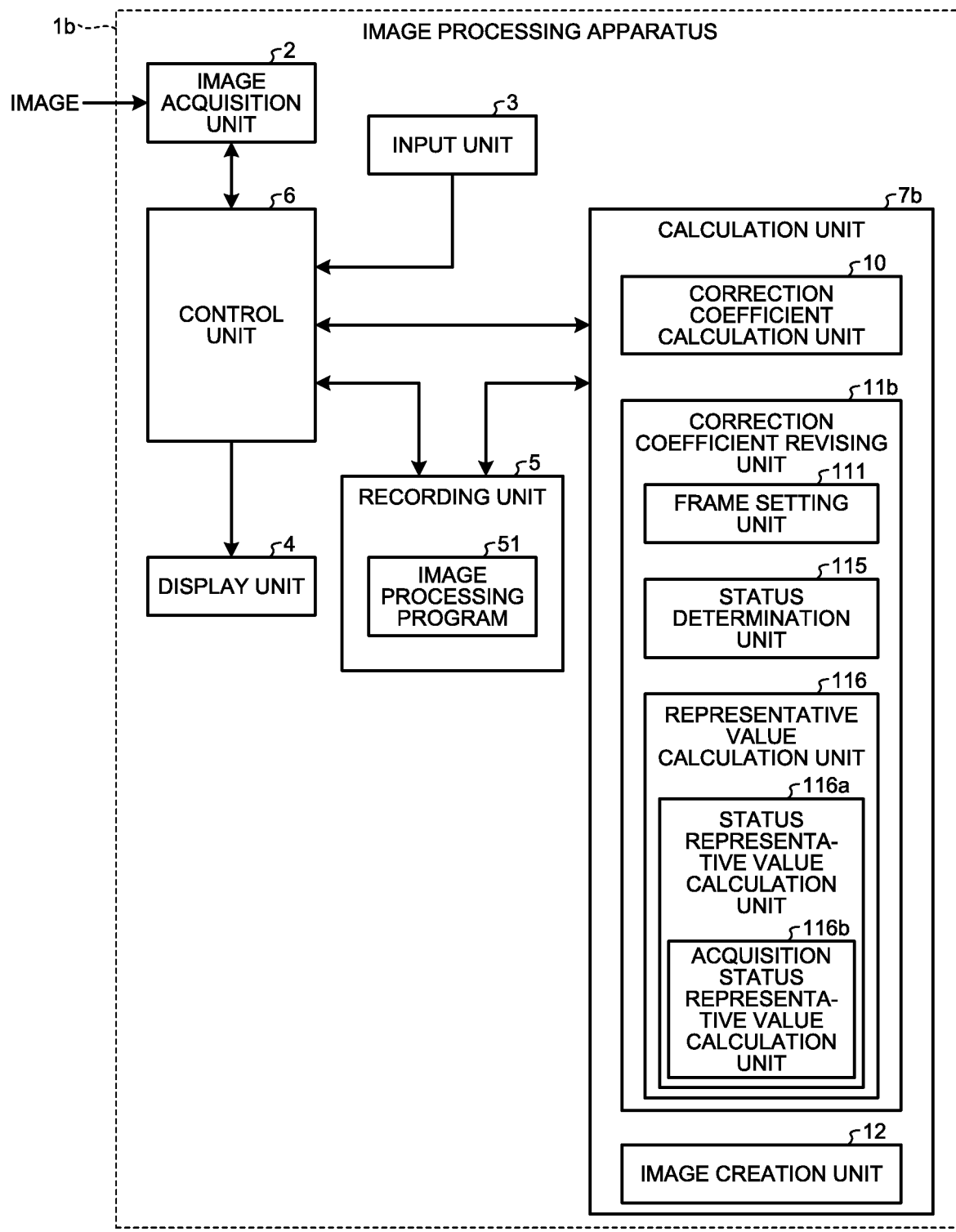
FIG. 17 is a block diagram illustrating a configuration of an image processing apparatus according to a third embodiment of the present disclosure.

FIG. 17 is a block diagram illustrating a configuration of the image processing apparatus according to the third embodiment of the present disclosure. An image processing apparatus 1b illustrated in FIG. 17 includes a calculation unit 7b in place of the calculation unit 7 of the image processing apparatus 1 according to the above-described first embodiment.

The calculation unit 7b is implemented by a CPU or the like. The calculation unit 7b reads the image processing program 51 recorded in the recording unit 5 and executes image processing of generating a display image on the basis of an image group.

Detailed Configuration of Calculation Unit

Next, a detailed configuration of the calculation unit 7b will be described.

The calculation unit 7b includes a correction coefficient revising unit 11b in place of the correction coefficient revising unit 11 of the calculation unit 7 according to the above-described first embodiment.

The correction coefficient revising unit 11b includes a frame setting unit 111, a status determination unit 115, and a representative value calculation unit 116.

The status determination unit 115 determines the acquisition timing of the image used for correction or the ease of acquisition of the correction coefficient.

The representative value calculation unit 116 calculates a representative value on the basis of the correction coefficient of the correction target frame and the correction coefficient of each of the plurality of frames. Furthermore, the representative value calculation unit 116 includes a status representative value calculation unit 116a that calculates a representative value on the basis of a determination result of the status determination unit 115. Furthermore, the status representative value calculation unit 116a includes an acquisition status representative value calculation unit 116b that calculates the representative value on the basis of the calculation result obtained by a status calculation unit 115a.

Processing in Image Processing Apparatus

Figure 18:
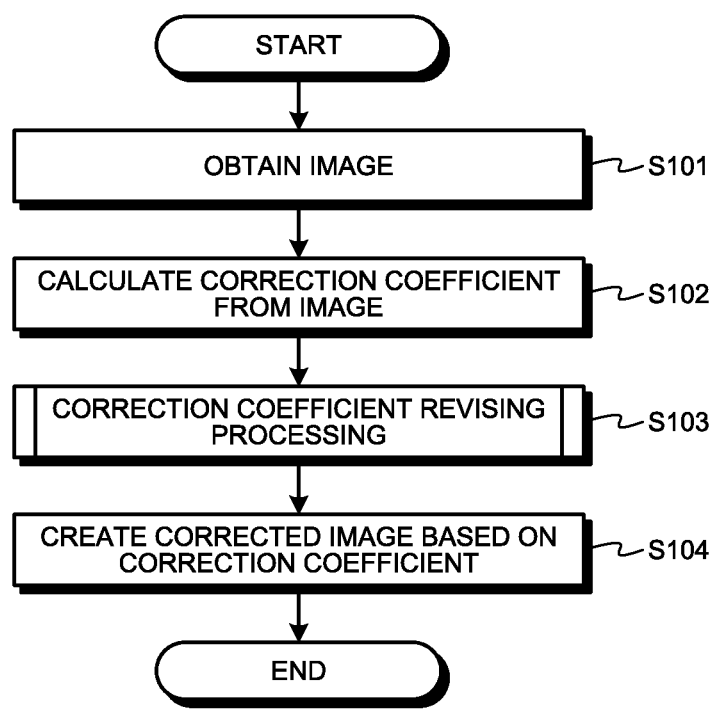
FIG. 18 is a flowchart illustrating an outline of image processing executed by the image processing apparatus according to the third embodiment of the present disclosure.

Next, an image processing method executed by the image processing apparatus 1b will be described. FIG. 18 is a flowchart illustrating an outline of processing executed by the image processing apparatus 1b. In FIG. 18, Steps S101, S102, and S104 respectively correspond to the above-described Steps S1, S2, and S4 of FIG. 2 described above, and thus, description will be omitted.

In Step S103, the correction coefficient revising unit 11b calculates a representative value on the basis of each of the correction coefficients of one or more frames of the time-series vicinity frame, and executes correction coefficient revising processing of performing revision by using the calculated representative value as a correction coefficient. After Step S103, the image processing apparatus 1b advances the process to Step S104.

Figure 19:
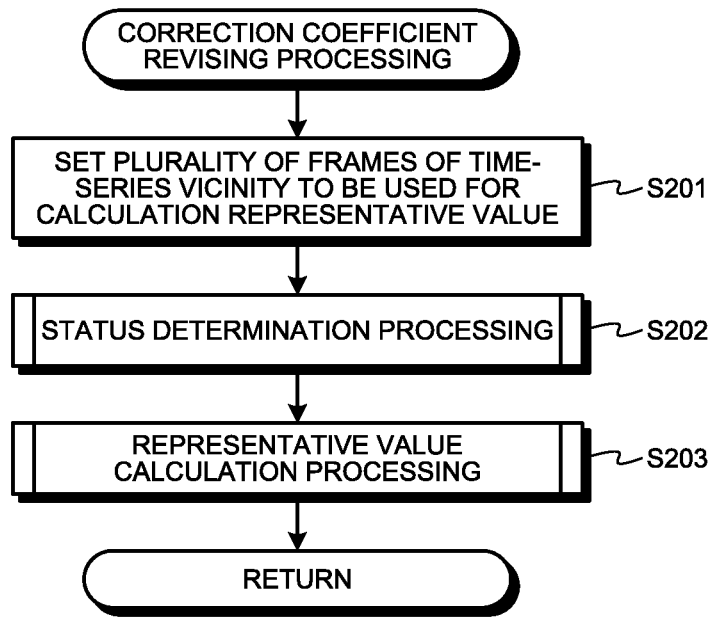
FIG. 19 is a flowchart illustrating an outline of correction coefficient revising processing in FIG. 18.

FIG. 19 is a flowchart illustrating an outline of correction coefficient revising processing of Step S103 in FIG. 18. Since Step S201 is similar to Step S11 in FIG. 3 described above, its description will be omitted.

In Step S202, the status determination unit 115 executes status determination processing of determining the status of an image used for revising a correction coefficient of the correction frame. After Step S202, the image processing apparatus 1b advances the process to Step S203.

Figure 20:
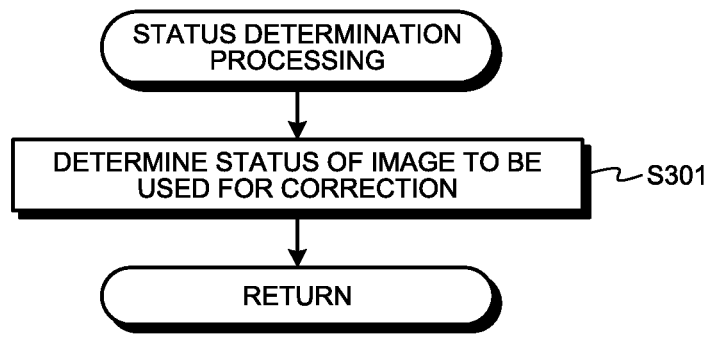
FIG. 20 is a flowchart illustrating an outline of status determination processing in FIG. 19.

FIG. 20 is a flowchart illustrating an outline of status determination processing of Step S202 in FIG. 19. As illustrated in FIG. 20, the status calculation unit 115a determines the status (acquisition timing) of an image to be used for revising the correction coefficient of the correction frame (Step S301). Specifically, the status calculation unit 115a determines the frame for grasping the acquisition timing on the basis of either an image as a correction target or an image in which information to be corrected appears with high contrast. After Step S301, the process returns to the correction coefficient revising processing of FIG. 19.

Returning to FIG. 19, Step S203 and beyond will be described.

In Step S203, the representative value calculation unit 116 calculates a representative value by using information based on the correction coefficient of the correction target frame and the correction coefficients of the time-series vicinity frames. After Step S203, the process 1b returns to the main routine in FIG. 18.

Figure 21:
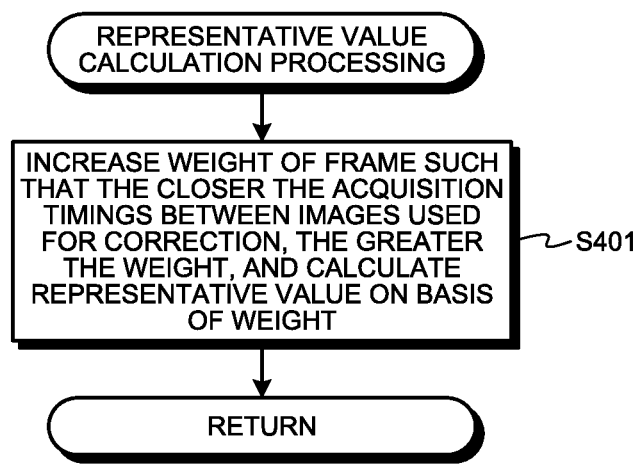
FIG. 21 is a flowchart illustrating an outline of representative value calculation processing in FIG. 19.

FIG. 21 is a flowchart illustrating an outline of representative value calculation processing in Step S203 in FIG. 19. As illustrated in FIG. 21, the status representative value calculation unit 116a increases the weight of a frame such that the closer the acquisition timings between images used for correction are, the greater the weight becomes, and calculates a representative value on the basis of the weight (Step S401). For example, when the status calculation unit 115a performs setting such that the weights for the vicinity frames of the image signal, that is, the frames to be one image which include the correction target frame with respect to the correction coefficient of the time-series vicinity frame of the correction coefficients of the frames are set to be great in a case, for example, where the image is generated by an endoscope of the sequential lighting system, and then multiplies the weights of the correction coefficients in individuals frame by the correction coefficients. Thereafter, the status representative value calculation unit 116a calculates the average value of the correction coefficients of the individual frames after the multiplication, as a representative value. After Step S401, the image processing apparatus 1b returns to the correction coefficient revising processing in FIG. 19.

According to the third embodiment of the present disclosure described above, it is possible to suppress blurring of the time-series image group.

First Modification of Third Embodiment

Next, a first modification of the third embodiment of the present disclosure will be described. The first modification of the third embodiment has a different representative value calculation processing executed by the image processing apparatus. Hereinafter, representative value calculation processing executed by the image processing apparatus according to the first modification of the third embodiment will be described. A same reference sign will be given to the configuration identical to the configuration of the image processing apparatus 1b according to the above-described third embodiment, and description for this will be omitted.

Figure 22:
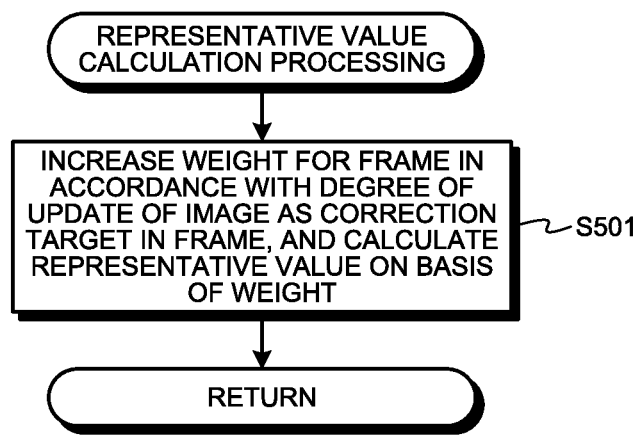
FIG. 22 is a flowchart illustrating an outline of representative value calculation processing according to a first modification of the third embodiment of the present disclosure.

FIG. 22 is a flowchart illustrating an outline of representative value calculation processing executed by the image processing apparatus 1b according to the first modification of the third embodiment. As illustrated in FIG. 22, the status representative value calculation unit 116a increases the weight for a frame in accordance with the degree of update of the image as a correction target in the frame, and calculates a representative value on the basis of the weight (Step S501). When the image as a correction target is updated, there is a possibility that the status has changed from the time of the previous update (for example, brightness change). At this time, the past correction coefficient might have been calculated in the status before the change. Therefore, the status representative value calculation unit 116a increases the weight for a frame in accordance with the degree of update of the image as a correction target in the frame, and then multiplies the weights of the correction coefficients of the individual frames by the correction coefficients, and thereafter calculates the average value of the correction coefficients of the individual frames after multiplication, as a representative value. After Step S501, the process returns to the correction coefficient revising processing in FIG. 19.

According to the first modification of the third embodiment of the present disclosure described above, it is possible to suppress blurring of the time-series image group.

Second Modification of Third Embodiment

Next, a second modification of the third embodiment of the present disclosure will be described. The second modification of the third embodiment has a different representative value calculation processing executed by the image processing apparatus. Hereinafter, representative value calculation processing executed by the image processing apparatus according to the second modification of the third embodiment will be described. A same reference sign will be given to the configuration identical to the configuration of the image processing apparatus 1b according to the above-described third embodiment, and description for this will be omitted.

Figure 23:
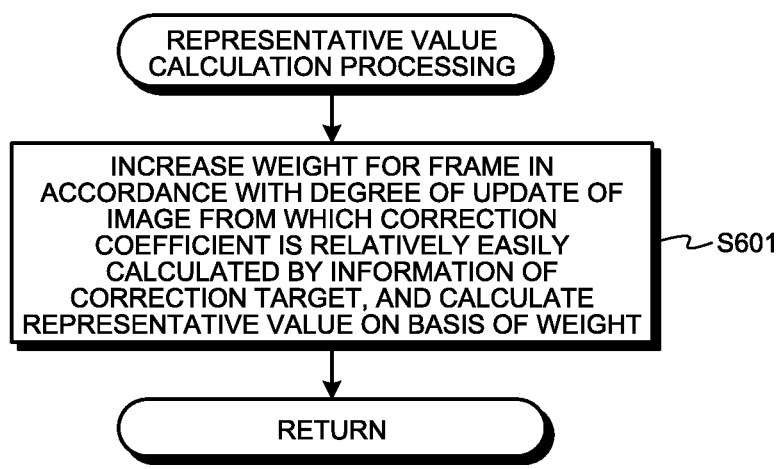
FIG. 23 is a flowchart illustrating an outline of representative value calculation processing according to a second modification of the third embodiment of the present disclosure.

FIG. 23 is a flowchart illustrating an outline of representative value calculation processing executed by the image processing apparatus 1b according to the second modification of the third embodiment. As illustrated in FIG. 23, the status representative value calculation unit 116a increases the weight for a frame in accordance with the degree of update of the image as a correction target in which information is represented in high contrast in the frame, and calculates a representative value on the basis of the weight (Step S601). When the image as a correction target is updated, there is a possibility that the status has changed from the time of the previous update (for example, contrast change). At this time, the past correction coefficient might have been calculated in the status before the change. Therefore, the status representative value calculation unit 116a increases the weight for a frame in accordance with the degree of update of the image as a correction target in which information is represented in high contrast in the frame, and then multiplies the weights of the correction coefficients of the individual frames by the correction coefficients, and thereafter calculates the average value of the correction coefficients of the individual frames after multiplication, as a representative value. After Step S601, the process returns to the correction coefficient revising processing in FIG. 19.

According to the second modification of the third embodiment of the present disclosure described above, it is possible to suppress blurring of the time-series image group.

Third Modification of Third Embodiment

Next, a third modification of the third embodiment of the present disclosure will be described. An image processing apparatus according to the third modification of the third embodiment is different in configuration, the status determination processing, and the representative value calculation processing, compared with the image processing apparatus 1b according to the above-described third embodiment. Hereinafter, the configuration of the image processing apparatus according to the third modification of the third embodiment will be first described and thereafter the status determination processing and the representative value calculation processing executed by the image processing apparatus according to the third modification of the third embodiment will be described. A same reference sign will be given to the configuration identical to the configuration of the image processing apparatus 1b according to the above-described third embodiment, and description for this will be omitted.

Configuration of Image Processing Apparatus

Figure 24:
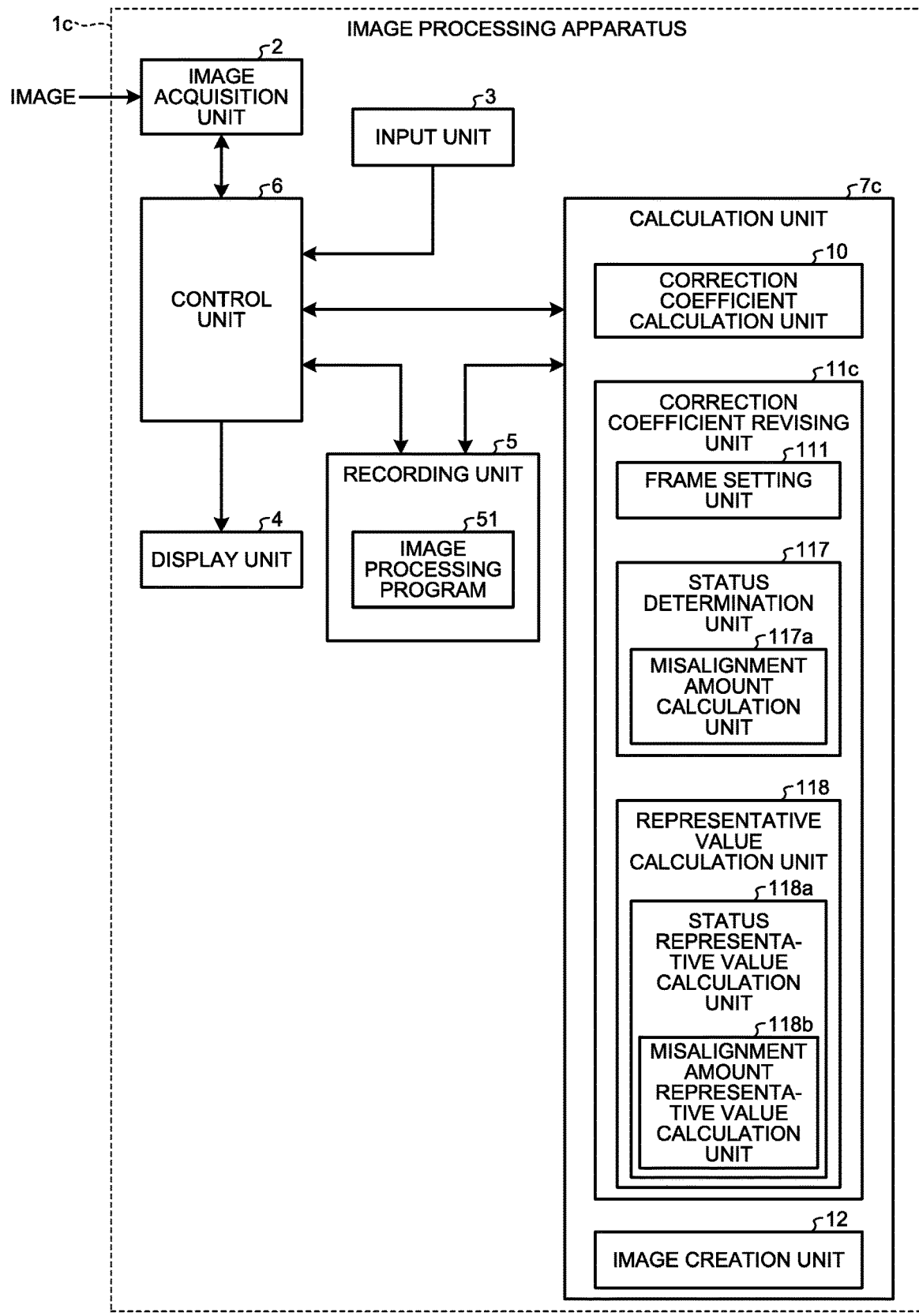
FIG. 24 is a block diagram illustrating a configuration of an image processing apparatus according to a third modification of the third embodiment of the present disclosure.

FIG. 24 is a block diagram illustrating a configuration of an image processing apparatus according to the third modification of the third embodiment of the present disclosure. An image processing apparatus 1c illustrated in FIG. 24 includes a calculation unit 7c in place of the calculation unit 7b of the image processing apparatus 1b according to the above-described third embodiment.

The calculation unit 7c is implemented by a CPU or the like. The calculation unit 7c reads the image processing program 51 recorded in the recording unit 5 and executes image processing of generating a display image on the basis of an image group.

Detailed Configuration of Calculation Unit

Next, a detailed configuration of the calculation unit 7c will be described.

The calculation unit 7c includes a correction coefficient revising unit 11c in place of the correction coefficient revising unit 11b of the calculation unit 7 according to the above-described third embodiment.

The correction coefficient revising unit 11c includes a frame setting unit 111, a status determination unit 117, and a representative value calculation unit 118.

The status determination unit 117 determines the acquisition status of the image to be used for correction. Furthermore, the status determination unit 117 includes a misalignment amount calculation unit 117a that calculates a misalignment amount between images used for correction.

The representative value calculation unit 118 calculates a representative value on the basis of the correction coefficient of the correction target frame and the correction coefficients of one or more frames set by the frame setting unit 111. The representative value calculation unit 118 includes a status representative value calculation unit 118a that calculates a representative value on the basis of a determination result of the status determination unit 117. Furthermore, the status representative value calculation unit 118a includes a misalignment representative value calculation unit 118b that calculates weights for the correction coefficient of the correction target frame and the correction coefficient of each of the plurality of frames on the basis of the misalignment amount and calculates a representative value on the basis of the weight.

Processing in Image Processing Apparatus

Next, an image processing apparatus executed by the image processing apparatus 1c will be described. An image processing method executed by the image processing apparatus 1c differs merely in the status determination processing and the representative value calculation processing out of the individual processing in the image processing method executed by the image processing apparatus 1b according to the third embodiment described above. Therefore, in the following description, the status determination processing and the representative value calculation processing executed by the image processing apparatus 1c will be described.

Figure 25:
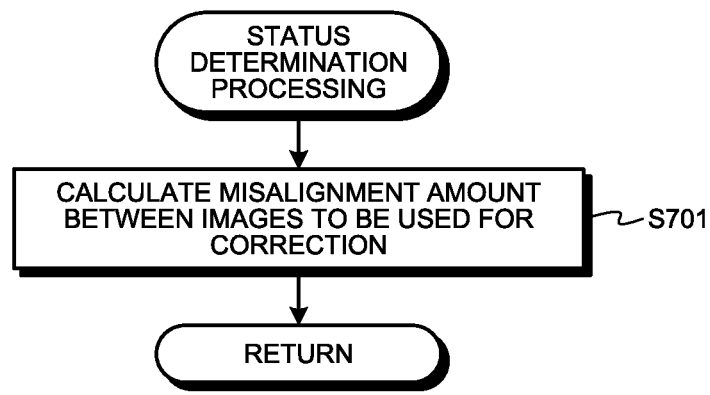
FIG. 25 is a flowchart illustrating an outline of status determination processing executed by the image processing apparatus according to the third modification of the third embodiment of the present disclosure.

FIG. 25 is a flowchart illustrating an outline of status determination processing executed by the image processing apparatus 1c. As illustrated in FIG. 25, the misalignment amount calculation unit 117a calculates a misalignment amount between images used for correction (Step S701). Specifically, the misalignment amount calculation unit 117a calculates the misalignment amount between individual images in accordance with a general technique, for example, by using a difference of movement vectors calculated on individual images, a movement amount detected by a gyro sensor or the like, when individual images are captured. In this case, when the movement amount by a gyro sensor or the like is used, the misalignment amount calculation unit 117a uses detection results of the gyro sensor or the like stored in the metadata or the header information of individual images to calculate the misalignment amount between individual images. After Step S701, the process returns to the correction coefficient revising processing in FIG. 19.

Figure 26:
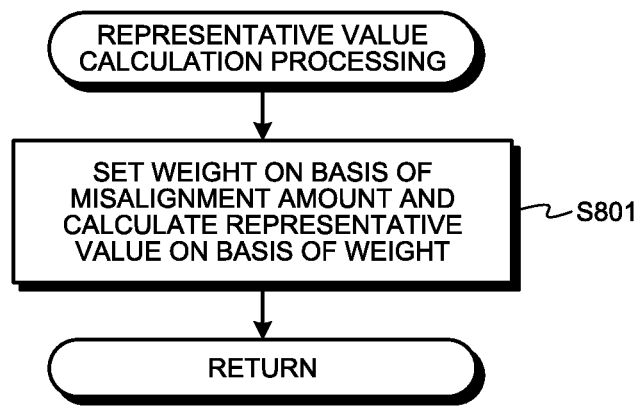
FIG. 26 is a flowchart illustrating an outline of representative value calculation processing executed by the image processing apparatus according to the third modification of the third embodiment of the present disclosure.

FIG. 26 is a flowchart illustrating an outline of representative value calculation processing executed by the image processing apparatus 1c. As illustrated in FIG. 26, the misalignment representative value calculation unit 118b sets a weight on the basis of the misalignment amount calculated by the misalignment amount calculation unit 117a, and calculates a representative value on the basis of the weight (Step S801). Specifically, when the misalignment amount between the correction target frame and the time-series vicinity frame is larger than a predetermined value, the image is considered to have greatly changed, and thus, there is no need to consider the correction coefficients of the time-series vicinity frames in the past earlier than the correction target frame. Accordingly, the misalignment representative value calculation unit 118b increases the weight of the correction target frame and reduces the weight of the correction coefficients of the time-series vicinity frames, so as to calculate the representative value. In contrast, when the misalignment amount between the correction target frame and the time-series vicinity frame is a predetermined value or less, the images are considered not to change greatly, and thus, the misalignment representative value calculation unit 118b calculates the representative value by equalizing the weights for the correction coefficients of the correction frame and each of the time-series vicinity frames. Note that, in the time-series vicinity frame, when the misalignment amount is larger than a predetermined value, the misalignment representative value calculation unit 118b may reduce the weight of the frame in which the misalignment amount is larger than the predetermined value, and together with this, when the misalignment amount is a predetermined value or less, the misalignment representative value calculation unit 118b may increase the weight of the frame in which the amount of misalignment is the predetermined value or less. After Step S801, the process returns to the correction coefficient revising processing of FIG. 19.

According to the third modification of the third embodiment of the present disclosure described above, it is possible to suppress blurring of the time-series image group.

Other Embodiments

The present disclosure can implement an image processing program recorded in a recording device by executing the program on a computer system such as a personal computer and a workstation. Furthermore, such a computer system may be used by connecting the computer system to another device including a computer system or a server via a local area network (LAN), a wide area network (WAN), or a public line such as the Internet. In this case, it is allowable to configure such that the image processing apparatus according to the first to third embodiments and the modifications of the embodiments obtains image data of an intraluminal image via these networks, outputs a result of image processing to various output devices such as a viewer and a printer, connected via these networks, and stores the result of image processing in a storage device connected via these networks, such as a recording medium that is readable by a reading device connected via a network.

In the flowcharts in this description, context of the processes among the steps is described by using expressions such as "first", "thereafter", and "subsequently", but the sequences of the processes needed for implementing the present disclosure are not intended to be uniquely defined by these expressions. In other words, the order of processing in the flowcharts described herein can be changed within a range implementable without contradiction.

The present disclosure is not limited to the first to third embodiments and the modifications of the embodiments, but various disclosures can be formed by appropriately combining a plurality of elements disclosed in the embodiments and the modification examples. For example, the disclosure may be formed by removing some elements from all the elements described in each of the embodiments and the modifications, or may be formed by appropriately combining elements described in different embodiments and modifications.

According to the present disclosure, it is possible to achieve an effect of suppressing blurring of a time-series image group.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general concept as defined by the appended claims and their equivalents.

What is claimed is:

1. An image processing apparatus comprising:
   a processor comprising hardware, the processor being configured to
   obtain a plurality of images that are temporally continuous, the plurality of images being generated by continuously imaging a subject illuminated with illumination light;
   calculate a correction coefficient on the basis of a correction target frame among the plurality of images;
   revise the correction coefficient of the correction target frame on the basis of the correction coefficient of each of a plurality of frames within a predetermined time set beforehand from a shooting time of the correction target frame; and
   create a display image on the basis of the correction target frame and the correction coefficient.

2. The image processing apparatus according to claim 1, wherein the plurality of images includes at least one of an image of the subject, the image being generated by imaging the subject under illumination of the illumination light having a predetermined wavelength band, and an image generated by imaging a living body lumen.

3. The image processing apparatus according to claim 1, wherein the processor is further configured to
   set the plurality of frames to be used for calculating a representative value of the correction coefficient; and
   calculate the representative value of the correction coefficient on the basis of the correction coefficient of the correction target frame and the correction coefficient of each of the plurality of frames, and
   set the representative value as a revised correction coefficient of the correction target frame.

4. The image processing apparatus according to claim 3, wherein the processor is further configured to calculate deviation of the correction coefficient of the correction target frame or one or more correction coefficients of the plurality of frames, with respect to the correction coefficient of a frame in a specific time-series section.

5. The image processing apparatus according to claim 4, wherein the processor is further configured to calculate a difference between the correction coefficient of the correction target frame and the one or more correction coefficients of the plurality of frames, as the deviation.

6. The image processing apparatus according to claim 4, wherein the processor is further configured to calculate the deviation from a distribution state of the correction coefficients based on the correction coefficient of each of the plurality of frames.

7. The image processing apparatus according to claim 6, wherein the processor is further configured to
   calculate one of median, an average value, and a Mahalanobis distance from the distribution state, and
   calculate a difference between the median or the average value and the correction coefficient of the correction target frame, as the deviation, or calculate the Mahalanobis distance, as the deviation.

8. The image processing apparatus according to claim 4, wherein the processor is further configured to calculate the representative value of the correction coefficient of the correction target frame on the basis of the deviation.

9. The image processing apparatus according to claim 8, wherein the processor is further configured to calculate weight of the correction target frame and weight of each of the plurality of frames with respect to the correction coefficient on the basis of the deviation, and calculate the representative value on the basis of the calculated weight.

10. The image processing apparatus according to claim 8, wherein the processor is further configured to calculate the representative value on the basis of the correction coefficient of each of the plurality of frames in a case where the deviation is greater than a predetermined value, and calculate a maximum value of the correction coefficients in the plurality of frames used for calculating the deviation, as the representative value, when the deviation is the predetermined value or less.

11. The image processing apparatus according to claim 3, wherein the processor is further configured to
    determine one of an acquisition timing of the image used for correction, and ease of acquisition of the correction coefficient, and
    calculate the representative value on the basis of a determination result by the determining.

12. The image processing apparatus according to claim 11, wherein the processor is further configured to determine an acquisition status of the image to be used for correction.

13. The image processing apparatus according to claim 12, wherein the processor is further configured to calculate the representative value on the basis of a determination result by the determining.

14. The image processing apparatus according to claim 13, wherein the processor is further configured to calculate weight of the correction target frame and weight of each of the plurality of frames with respect to the correction coefficient on the basis of a determination result by the determining, and calculate the representative value on the basis of the calculated weight.

15. The image processing apparatus according to claim 14, wherein processor is further configured to calculate the representative value with increased weight for the correction coefficient of each of the plurality of frames with respect to the correction coefficient, in accordance with a degree or possibility of being any one of a frame close to a shooting time of the correction target frame, a frame in which the image as a correction target has been updated, and a frame having an image in which information regarding the correction object appears in high contrast has been updated.

16. The image processing apparatus according to claim 11,
wherein the processor is configured to calculate a misalignment amount between images used for correction.

17. The image processing apparatus according to claim 16,
wherein the processor is further configured to calculate weight of the correction target frame and weight of each of the plurality of frames with respect to the correction coefficient on the basis of the misalignment amount, and calculate the representative value on the basis of the calculated weight.

18. The image processing apparatus according to claim 1, wherein the correction coefficient is a coefficient in enhancement of any one or more of tissues, mucosa, and a blood vessel in a living body, or a coefficient for combining images.

19. An image processing method to be executed by an image processing apparatus, the method comprising:
obtaining a plurality of images that are temporally continuous, the plurality of images being generated by continuously imaging a subject illuminated with illumination light;
calculating a correction coefficient for correcting each of the plurality of images on the basis of a correction target frame among the plurality of images;
revising the correction coefficient of the correction target frame on the basis of the correction coefficient of each of a plurality of frames within a predetermined time set beforehand from a shooting time of the correction target frame; and
creating a display image on the basis of the correction target frame and the correction coefficient.

20. A non-transitory computer readable recording medium storing a program that causes a computer to execute a process, the process comprising:
obtaining a plurality of images that are temporally continuous, the plurality of images being generated by continuously imaging a subject illuminated with illumination light;
calculating a correction coefficient for correcting each of the plurality of images on the basis of a correction target frame among the plurality of images;
revising the correction coefficient of the correction target frame on the basis of the correction coefficient of each of a plurality of frames within a predetermined time set beforehand from a shooting time of the correction target frame; and
creating a display image on the basis of the correction target frame and the correction coefficient.

* * * * *